United States Patent [19]

Stabel et al.

[11] Patent Number: 5,073,650

[45] Date of Patent: Dec. 17, 1991

[54] PREPARATION OF 1,4-BUTANEDIOL

[75] Inventors: Uwe Stabel, Edingen-Neckarhausen; Hans-Juergen Gosch, Bad Durkheim; Rolf Fischer, Heidelberg; Wolfgang Harder, Weinheim; Claus Hechler, Mannheim, all of Fed. Rep. of Germany

[73] Assignee: BASF Aktiengesellschaft, Ludwigshafen, Fed. Rep. of Germany

[21] Appl. No.: 672,671

[22] Filed: Mar. 20, 1991

[30] Foreign Application Priority Data

Mar. 21, 1990 [DE] Fed. Rep. of Germany ....... 4009029

[51] Int. Cl.$^5$ .................... C07C 29/149; C07C 31/20
[52] U.S. Cl. .................................................. 568/864
[58] Field of Search ......................................... 568/864

[56] References Cited

U.S. PATENT DOCUMENTS

| 2,772,292 | 11/1956 | McShane et al. | 568/864 |
|---|---|---|---|
| 2,772,293 | 11/1956 | Gilbert et al. | 568/864 |
| 2,975,218 | 3/1961 | Buchner et al. | 568/864 |
| 3,361,832 | 8/1963 | Pine et al. | |
| 4,010,197 | 3/1977 | Toriya et al. | 568/864 |
| 4,032,458 | 6/1977 | Cooley et al. | 568/864 |
| 4,155,919 | 5/1979 | Ramioulle | 568/864 |
| 4,268,695 | 5/1981 | Lange et al. | 568/864 |
| 4,550,185 | 10/1985 | Mabry et al. | 549/508 |
| 4,562,283 | 12/1985 | Schnabel et al. | 568/864 |
| 4,584,419 | 4/1986 | Sharif et al. | 568/864 |
| 4,609,636 | 9/1986 | Mabry et al. | 502/183 |
| 4,810,807 | 3/1989 | Budge et al. | 544/508 |
| 4,940,805 | 7/1990 | Fischer et al. | 568/864 |

FOREIGN PATENT DOCUMENTS

| 382050 | 8/1990 | European Pat. Off. |
| 1901870 | 9/1969 | Fed. Rep. of Germany. |
| 2543673 | 4/1976 | Fed. Rep. of Germany. |
| 2519817 | 11/1976 | Fed. Rep. of Germany. |
| 2321101 | 7/1982 | Fed. Rep. of Germany. |
| 1226292 | 3/1971 | United Kingdom. |
| 1454440 | 11/1976 | United Kingdom. |
| 1551741 | 8/1979 | United Kingdom. |

Primary Examiner—J. E. Evans
Attorney, Agent, or Firm—John H. Shurtleff

[57] ABSTRACT

A process for the preparation of 1,4-butanediol by catalytically hydrogenating maleic anhydride in the presence of an alcohol, at elevated temperature and elevated pressure and with the aid of a cobalt-containing catalyst comprises partially hydrogenating the reaction mixture in a first hydrogenation step at from 100° to 200° C. and at from 30 to 200 bar and subsequently post-hydrogenating the product of this first hydrogenation step, without further work-up at higher temperature and pressure than in the first hydrogenation step, in a second hydrogenation step at from 200° to 300° C. and at from 200 to 350 bar.

8 Claims, 1 Drawing Sheet

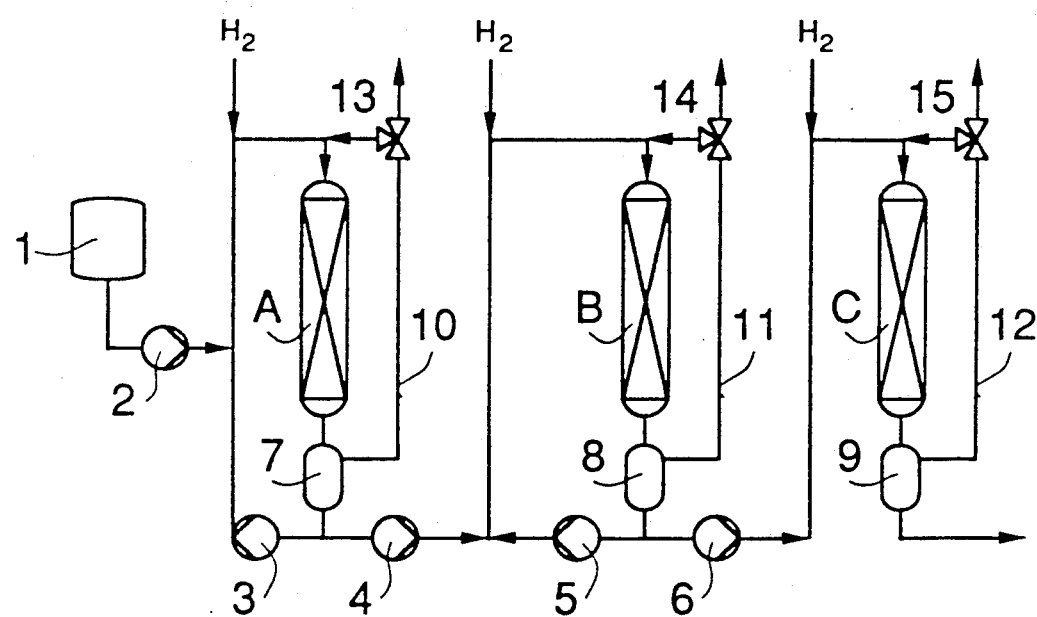

PREPARATION OF 1,4-BUTANEDIOL

The present invention relates to a process for the preparation of 1,4-butanediol by catalytically hydrogenating maleic anhydride in the presence of an alcohol with the aid of a cobalt-containing catalyst.

It is known that 1,4-butanediol (BD) can be prepared by catalytically hydrogenating maleic anhydride (MA) in the presence of an alcohol Thus, U.S. Pat. No. 4,268,695 describes the one-step hydrogenation of solutions of MA in monohydric, aliphatic alcohols in the presence of copper chromite catalysts at from 180° to 300° C. and at from 250 to 350 bar to give 1,4-butanediol.

U.S. Pat. No. 4,940,805 discloses the one-step hydrogenation of MA in the presence of aliphatic alcohols with the aid of cobalt-containing catalysts at from 100° to 350° C. and at from 50 to 350 bar. Although both processes give good to very good butanediol yields on a laboratory scale, scale-up to an industrial scale has, however, hitherto presented considerable difficulties due to the large amount of heat of hydrogenation which is liberated, which can only be dissipated with difficulty and results in a loss in selectivity in the reaction and in damage to the catalyst.

U.S. Pat. No. 4,584,419 describes a process for the preparation of BD by catalytically hydrogenating the di-$C_1$- to $C_3$-alkyl esters of $C_4$-dicarboxylic acids with the aid of a copper chromite catalyst, in which these esters are first partially hydrogenated in a first hydrogenation step at from 170° to 190° C. and subsequently post-hydrogenated in a second hydrogenation step at from 160° to 175° C., in both cases at from 25 to 75 bar. The particular disadvantage of this process is that the dicarboxylates used as starting materials must first be generated in a separate reaction, for example by esterifying MA, making this process uneconomical.

It is therefore an object of the present invention to provide a process for the hydrogenation of MA to give BD, which is economical, can be used on an industrial scale and, in particular, makes possible good BD selectivity and a long service life of the catalyst at a high weight hourly space velocity.

We have found that this object is achieved by a process for the preparation of 1,4-butanediol by catalytically hydrogenating maleic anhydride in the presence of an alcohol, at elevated temperature and elevated pressure and with the aid of a cobalt-containing catalyst, which comprises partially hydrogenating the reaction mixture in a first hydrogenation step at from 100° to 200° C. and at from 30 to 200 bar and subsequently post-hydrogenating the product of this first hydrogenation step, without further work-up at higher temperature and pressure than in the first hydrogenation step, in a second hydrogenation step at from 200° to 300° C. and at from 200 to 350 bar.

When dissolved in an alcohol, MA (I) reacts, even during the dissolution process, virtually quantitatively with addition of an alcohol molecule to give the monomaleate II concerned (see Equation (1)).

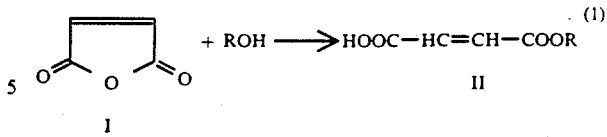

Thus, the actual substrate to be hydrogenated in the hydrogenation of MA solutions in alcohols is thus the monoester II. The hydrogenation presumably involves first hydrogenation of the double bond of the monomaleate (cf. equation (2)), giving the monosuccinate III concerned:

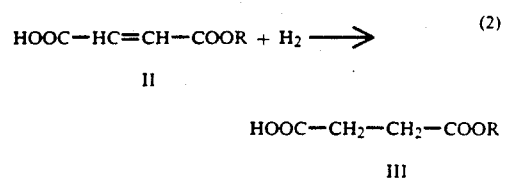

As the hydrogenation continues, the monosuccinate III is hydrogenated consuming 4 moles of hydrogen per mole of III to give BD IV (cf. equation (3)):

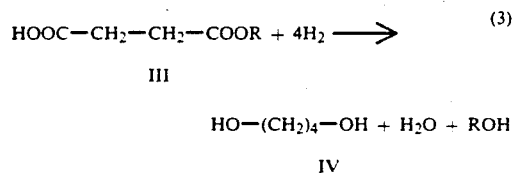

The alcohol ROH liberated during this hydrogenation can be removed by distillation and recycled into the reaction to dissolve the MA or, more precisely, to generate the monomaleate II. The hydrogenation of MA in the presence of an alcohol thus proceeds in accordance with the overall equation (4):

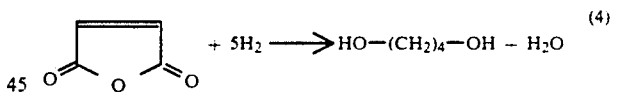

As a byproduct of this reaction, tetrahydrofuran (THF) can form either by subsequent cyclization of BD or by direct hydrogenation of the γ-butyrolactone (GBL) which occurs as an intermediate in the reaction mixture.

In the process according to the invention, MA can be used in solid, liquid or gaseous form. For the hydrogenation, it is dissolved in the particular alcohol ROH, expediently at from 20° C. (room temperature) to 100° C., preferably at from 30° to 70° C. It is particularly advantageous to employ gaseous MA, as generally obtained on an industrial scale in the catalytic oxidation of butane, butene or aromatic hydrocarbons. The gaseous MA can be absorbed into the particular alcohols, for example by the process of U.S. Pat. No. 4,562,283. The water present in technical-grade MA can be particularly easily separated off in this procedure, for example by simple azeotropic distillation. However, it is also possible to hydrogenate the resultant absorbate without removing the water.

It is of course also possible to replace the MA solution in an alcohol in the hydrogenation by a monoand/or diester of maleic acid or fumaric acid. Such mixtures may contain, as further constituents, GBL, succinic acid and/or the mono- or diesters thereof. The use of starting materials of this type is equivalent to the use of MA/alcohol solutions in the process according to the invention.

The hydrogenation according to the invention can be carried out in the presence of a wide variety of alcohols, either monohydric or polyhydric, primary, secondary or tertiary, aliphatic or cycloaliphatic. However, preference is given to the use of monohydric, aliphatic alcohols having 1 to 6 carbon atoms, such as methanol, ethanol, propanol, isopropanol, n-butanol, isobutanol or hexanols. The use of butanols is particularly advantageous since the removal of the water formed during the hydrogenation from the hydrogenation product by azeotropic distillation can be carried out particularly simply and effectively in their presence.

The MA is expediently dissolved in the particular alcohol in a molar ratio of from. 1:0.1 to 1:30, preferably from 1:0,5 to 1:20, particularly preferably from 1:1 to 1:10.

According to the invention the MA solution in the particular alcohol is first hydrogenated in a first step at from 100° to 200° C., preferably at from 150° to 200° C., and at from 30 to 200 bar, preferably at from 70 to 150 bar. The weight hourly space velocity can generally be from 0.1 to 10, in particular from 1 to 7 kg of MA/l of catalyst per hour.

The product of the hydrogenation of the first step generally comprises a mixture of the monosuccinate and disuccinate concerned, the particular alcohol and water. The disuccinate is produced, together with the water, under the hydrogenation conditions used depending on the weight hourly space velocity. In general, the amount of disuccinate formed in the hydrogenation product decreases with increasing space velocity. In addition to said succinates, the hydrogenation product from the first hydrogenation step may also contain small amounts (usually up to 10 mol %), based on the MA employed, of unsaturated monoesters and diesters of maleic acid and fumaric acid. GBL, THF or BD are generally only formed in small amounts, if at all, in the first hydrogenation step.

The product from the first hydrogenation step is, according to the invention, fed to the second hydrogenation step without work-up.

In the second hydrogenation step, the product from the first hydrogenation step is hydrogenated, according to the invention, at 220° to 300° C., preferably at from 230° to 260° C., and at from 200 to 350 bar, preferably at from 220 to 300 bar. The weight hourly space velocity can be from 0.05 to 0.9, in particular from 0.2 to 0.7, kg of MA/l of catalyst per hour.

The product from the second hydrogenation step essentially comprises a mixture of BD, THF, water and a particular alcohol, and may also contain unreacted GBL or succinates.

The useful products can be isolated from the hydrogenation product by conventional work-up methods, but expediently by distillation. The incompletely hydrogenated intermediates of MA hydrogenation, such as succinates, GBL and THF, can be isolated and used for the usual applications of the products, but are advantageously fed back to the hydrogenation. The hydrogen required for the hydrogenation of MA to give BD can be metered to the reactor in a stoichiometric amount, but expediently an excess of hydrogen is employed in both hydrogenation steps The extent of the excess of hydrogen is generally not crucial since the unconsumed hydrogen is circulated and fed back to the hydrogenation. If desired, some of the hydrogen can be burnt off as offgas.

The hydrogenations int he first and second steps can each be carried out in one or more reactors. In the context of the present invention, the term hydrogenation step thus means the hydrogenation under the conditions of a certain temperature and pressure range The hydrogenation reaction in a hydrogenation step can thus extend over a plurality of reactors, i.e. the apparatus for a hydrogenation step can comprise a plurality of reactors.

The process according to the invention can be carried out batchwise or, preferably, continuously. In the continuous procedure, tubular or tube-bundle reactors can be advantageously employed, using the pool or trickle procedure. The reactors may be provided with conventional means for regulating the temperature, i.e. for heating and cooling, externally or internally. A further possibility for regulating the temperature is recycling unconsumed hydrogen or some of the hydrogenation product from the second step into the hydrogenation.

The catalysts can be used in suspended form, but the fixed-bed arrangement of the catalysts is preferred.

In principle, any catalyst which is suitable for the hydrogenation of maleic anhydride, maleic acid, fumaric acid and the monoesters and diesters of these acids to give BD can be used in the process according to the invention. Catalysts of this type are described, for example, in DE-A 25 19 817, U.S. Pat. No. 4,550,185, U.S. Pat. No. 4,609,636, U.S. Pat. No. 4,268,695, U.S. Pat. No. 4,810,807 and DE-A 19 01 870.

Particularly suitable catalysts for the process according to the invention are those which contain cobalt and at least one of the elements manganese, copper and/or phosphorus. Preference is given to catalysts which, in addition to cobalt, contain at least two of the elements manganese, copper, phosphorus and/or molybdenum. Catalysts which contain, in addition to cobalt, at least three of the elements manganese, copper, phosphorus, molybdenum and/or sodium have particularly advantageous properties in the process according to the invention. Catalysts of this type are known and are described in DE-A 23 21 101 and in U.S. patent application Ser. No. 07/471543. Examples of advantageous catalysts in the process according to the invention are those whose catalytically active material comprises at least 40% by weight of cobalt (calculated as Co) and contains, as further catalytically active constituents, up to 10% by weight, preferably from 3 to 7% by weight, of manganese (calculated as Mn), up to 20% by weight, preferably from 0.1 to 5% by weight, of phosphoric acid ($H_3PO_4$) and up to 1% by weight, preferably from 0.01 to 0.5% by weight, of sodium (calculated as Na). Particular preference is given to those of the abovementioned catalysts whose catalytically active material contains, as additional catalytically active constituents, up to 30% by weight, preferably from 12 to 18% by weight, of copper (calculated as Cu) and up to 5% by weight, preferably from 1 to 4% by weight, of molybdenum (calculated as Mo).

The catalysts used according to the invention can be used in the process according to the invention either in the form of supported catalysts or preferably in compact form, i.e. without a carrier. The nature of the carrier material is generally not crucial, and conventional carrier materials such as silica, alumina, titanium dioxides, activated charcoal, silicates or zeolites can be used If necessary, binders and molding assistants can also be used to prepare the catalysts.

The catalysts are preferably activated with hydrogen before use in the process according to the invention. The majority of the catalytically active catalyst constituents, which are generally in the form of their oxides after the calcination, are reduced, generally to give the corresponding metals. Further details on the preparation of these catalysts are given in DE-A 23 21 101 and in U.S. patent application Ser. No. 07/471543.

The two-step hydrogenation process according to the invention for the preparation of BD from MA makes it possible to dissipate up to 50% of the heat of hydrogenation produced, at lower temperatures than in the one-step process. This reduces the risk of the formation of hot spots, which exists, in particular, at high hydrogenation temperatures and high space velocities, and increases the selectivity and service life of the catalyst, in particular when the process is carried out on an industrial scale.

EXAMPLE 1

The hydrogenation was carried out using a hydrogenation plant as shown in the attached drawing.

0.49 kg of catalyst was installed in the reactor tube A of the reactor cascade shown diagrammatically in the drawing. The length of the reactor tube was 2000 mm and its internal diameter was 30 mm. The catalyst used contained the following catalytically active constituents: 63.4% by weight of cobalt, calculated as CoO, 18.1% by weight of copper, calculated as CuO, 6.8% by weight of manganese, calculated as $Mn_3O_4$, 3.1% by weight of molybdenum, calculated as $MoO_3$, 0.15% by weight of sodium, calculated as $Na_2O$ and 3.3% by weight of phosphorus, calculated as $H_3PO_4$. The catalyst comprised extruded pellets 4 mm in thickness. 1.49 kg of the above-described catalyst were installed in the reactor tube B of the cascade, having a length of 2000 mm and internal diameter of 30 mm, and 0.38 kg was installed in the reactor tube C, having a length of 2000 mm and an internal diameter of 16 mm.

The reduction of the catalyst was carried out separately in each reactor tube. To this end, the tubes were heated to 290° C. at a heating rate of 20° C./min while passing in 300 1/h of nitrogen. The nitrogen was subsequently slowly replaced by hydrogen over the course of 6 hours The temperature was then increased to from 300° to 310° C., and 300 1/h of pure hydrogen were passed over the catalyst at this temperature for 48 hours.

The first hydrogenation step was carried out in reactor A, and the second hydrogenation step was carried out in reactors B and C. For the hydrogenation, a mixture of MA and n-butanol in a molar ratio of 1:2.5 and in an amount of 1.23 kg/h was passed, after the catalyst had been reduced, into the hydrogenation circuit of reactor A together with hydrogen, from the tank (1) by means of the feed pump (2). The product from the first hydrogenation step was fed, with level control, from reactor A into the hydrogenation circuit of reactor B by means of the pump (4) via the gas/liquid separator (7). The hydrogenation product from reactor B was transported, with level control, into reactor C with the aid of the pump (6) via the gas/liquid separator (8). The hydrogenation product from reactor C was discharged via the gas/liquid separator (9). The pumps (3) and (5) provided circulation of the reaction mixture in the hydrogenation circuits of reactors A (hydrogenation step 1) and B (1st part of hydrogenation step 2). The hydrogen, after separation from the liquid reaction mixture via the three gas/liquid separators (7), (8) and (9), was fed back into reactors A, B and C respectively via lines (10), (11) or (12) respectively and valves (13), (14) or (15) respectively, or discharged as offgas In the present example, the hydrogen was metered separately into each reactor, the excess hydrogen was purged via the particular separators and burnt off as offgas The reactor tubes were heated by electrical block heaters.

The reaction conditions were as follows:

TABLE 1

| Reaction Conditions | | | |
|---|---|---|---|
| | Reactor A | Reactor B | Reactor C |
| Pressure (bar) | 100 | 230 | 260 |
| Temperature (°C.) | 190 | 260 | 260 |
| Amount of offgas (1/h) | 110 | 400 | 300 |
| Circulated amount (1/h) | 10 | 10 | — |
| Amount of hydrogen (1/h) | 220 | 780 | 360 |

In reactor A the weight hourly space velocity over the catalyst of 1.74 kg of MA/l of catalyst per hour, based on the amount of MA fed in. For the second hydrogenation step, i.e. reactors B and C, the weight hourly space velocity was 0.45 kg of MA/l of catalyst per hour under the conditions used, based on the entire catalyst volume in reactors B and C. The space velocity of the entire catalyst volume in both hydrogenation steps was 0.36 kg of MA/l of catalyst per hour.

Analysis of the hydrogenation products by gas chromatography gave the following composition:

TABLE 2

| Composition of the Hydrogenation Products from the First and Second Hydrogenation Steps | | |
|---|---|---|
| | After reactor A | After reactor C |
| Dibutyl succinate | 15.4 mol-% | 6.9 mol-% |
| Monobutyl succinate | 84.6 mol-% | 0.3 mol-% |
| Butanediol (BD) | 0.0 mol-% | 68.9 mol-% |
| γ-Butyrolactone (GBL) | 0.0 mol-% | 10.6 mol-% |
| THF | 0.0 mol-% | 8.4 mol-% |

The conversion to BD, GBL and THF was thus 87.9 mol-%. Taking into account the recycling of the succinates into the hydrogenation, the following formula:

$$\text{Overall selectivity} = \frac{\text{mol of BD} + \text{mol of GBL} + \text{mol of THF}}{\text{mol MA} - \text{mol of succinates}} \cdot 100$$

gives an overall selectivity for BD, GBL and THF of 94.4%.

COMPARATIVE EXAMPLE

Reactor tubes A, B, and C of the apparatus in Example 1 were charged as follows with the catalyst of Example 1: Reactor tubes A and B each with 1.38 kg, Reactor tube C with 0.36 kg.

The catalyst was subsequently reduced as described in Example 1. After the reduction, a mixture of MA in n-butanol in the molar ratio of 1:2.5 and in an amount of 1 kg/h was fed into the reactor cascade. All three reactors were kept at from 240° to 260° C. and from 200 to 260 bar. Otherwise, the hydrogenation apparatus was operated as described in Example 1.

TABLE 3

| | Reaction Conditions | | |
|---|---|---|---|
| | Reactor A | Reactor B | Reactor C |
| Pressure (bar) | 200 | 230 | 260 |
| Temperature (°C.) | 240 | 240 | 260 |
| Amount of offgas (1/h) | 300 | 300 | 300 |
| Circulated amount (1/h) | 10 | 10 | — |
| Amount of hydrogen (1/h) | 410 | 610 | 340 |

The weight hourly space velocity of the catalyst in reactor A was 0.5 kg of MA/1 of catalyst per hour, based on the amount of MA fed in. The space velocity of the entire catalyst volume in the hydrogenating apparatus was 0.22 kg of MA/1 of catalyst per hour.

Analysis of the hydrogenation products from reactors A and C by gas chromatography gave the following composition:

TABLE 4

| Compositions of the Hydrogenation Products from Reactors A and C | | |
|---|---|---|
| | After reactor A | After reactor C |
| Dibutyl succinate | 20.5 mol-% | 3.0 mol-% |
| Monobutyl succinate | 34.6 mol-% | 0.1 mol-% |
| Butanediol (BD) | 10.0 mol-% | 61.6 mol-% |
| γ-Butyrolactone (GBL) | 22.3 mol-% | 4.5 mol-% |
| THF | 12.7 mol-% | 21.0 mol-% |

Taking into account the recycling of the succinates into the hydrogenation, this gives an overall selectivity for BD, GBL and THF of 89.8%.

The conclusion from this is that the hydrogenation of MA in two hydrogenation steps as in Example 1 gives a higher overall selectivity than the hydrogenation of MA in only one hydrogenation step, in spite of a higher space velocity.

We claim:

1. A process for the preparation of 1,4-butanediol by catalytically hydrogenating maleic anhydride in the presence of an alcohol, at elevated temperature and elevated pressure and with the aid of a cobalt-containing catalyst, which comprises partially hydrogenating the reaction mixture in a first hydrogenation step at from 100° to 200° C. and at from 30 to 200 bar and subsequently post-hydrogenating the product of this first hydrogenation step, without further work-up at higher temperatures and pressure than in the first hydrogenation step, in a second hydrogenation step at from 200° to 300° C. and at from 200 to 350 bar.

2. A process as claimed in claim 1, wherein the catalyst used contains cobalt and at least one of the elements manganese, copper and/or phosphorus.

3. A process as claimed in claim 1, wherein the catalyst used contains cobalt and at least two of the elements manganese, copper, phosphorus and/or molybdenum.

4. A process as claimed in claim 1, wherein the catalyst used contains cobalt and at least three of the elements manganese, copper, phosphorus, molybdenum and/or sodium.

5. A process as claimed in claim 1, wherein the active material of the catalyst comprises at least 40% by weight of cobalt (calculated as Co).

6. A process as claimed in claim 1, wherein a catalyst is used whose active material comprises at least 40% by weight of cobalt (calculated as Co) and which contains, as further catalytically active constituents, up to 10% by weight of manganese (calculated as Mn), up to 20% by weight of phosphoric acid and up to 1% by weight of sodium (calculated as Na).

7. A process as claimed in claim 1, wherein a catalyst is used whose active material comprises at least 40% by weight of cobalt (calculated as Co) and which contains, as further catalytically active constituents, up to 10% by weight of manganese (calculated as Mn), up to 30% by weight of copper (calculated as Cu), up to 5% by weight of molybdenum (calculated as Mo), up to 20% by weight of phosphoric acid and up to 1% by weight of sodium (calculated as Na).

8. A process as claimed in claim 1, wherein the alcohol used is n-butanol.

* * * * *